(12) United States Patent
Cheng et al.

(10) Patent No.: US 11,452,472 B2
(45) Date of Patent: Sep. 27, 2022

(54) MINIATURIZED SENSING PROBE AND MANUFACTURING METHOD THEREOF

(71) Applicant: National Chiao Tung University, Hsinchu (TW)

(72) Inventors: Yu-Ting Cheng, Hsinchu (TW); Erh-Chieh Liang, Hsinchu (TW); Kun-Lin Tsou, Hsinchu (TW); Yih-Sharng Chen, Hsinchu (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 509 days.

(21) Appl. No.: 16/671,652

(22) Filed: Nov. 1, 2019

(65) Prior Publication Data

US 2020/0337605 A1    Oct. 29, 2020

(30) Foreign Application Priority Data

Apr. 25, 2019  (TW) ................................ 108114558

(51) Int. Cl.
*A61B 5/1473* (2006.01)
*A61B 5/145* (2006.01)
*A61B 5/0205* (2006.01)

(52) U.S. Cl.
CPC ........ *A61B 5/1473* (2013.01); *A61B 5/02055* (2013.01); *A61B 5/14539* (2013.01); *A61B 5/14546* (2013.01); *A61B 2560/0468* (2013.01); *A61B 2560/063* (2013.01); *A61B 2562/0209* (2013.01); *A61B 2562/0233* (2013.01);

(Continued)

(58) Field of Classification Search
CPC .............. A61B 5/1473; A61B 5/14539; A61B 5/14546; A61B 2562/063; A61B 2562/164; A61B 2560/0468
See application file for complete search history.

(56) References Cited

U.S. PATENT DOCUMENTS

2016/0146754 A1 * 5/2016 Prasad ................. A61B 5/1477
204/547

OTHER PUBLICATIONS

Liang et al., "A pH and Temperature Sensing Needle for Muscle Tissue Ischemia Monitoring," 22$^{nd}$ International Conference on Miniaturized Systems for Chemistry and Life Sciences, Nov. 11-15, 2018, pp. 1999-2001, 3 pages.

(Continued)

*Primary Examiner* — Puya Agahi
(74) *Attorney, Agent, or Firm* — Muncy, Geissler, Olds & Lowe, P.C.

(57) ABSTRACT

A miniaturized sensing probe and a manufacturing method thereof are provided. The miniaturized sensing probe includes: a probe substrate including a probe part and a circuit connection part; a sensor disposed on the probe part and electrically connected to the circuit connection part; and a needle unit used to accommodate the probe part of the probe substrate; wherein the sensor performs sensing when placed into an analyte through the needle unit and transmits a sensing signal through the circuit connection part. The miniaturized sensing probe of the present invention may be easily placed into the analyte without the use of other instrument or surgery. This means is of benefit to a clinician performing an early diagnosis on a patient with a peripheral vascular disease or monitoring the biological value of the muscle during surgery in real time.

9 Claims, 18 Drawing Sheets

(52) U.S. Cl.
CPC ..... *A61B 2562/063* (2013.01); *A61B 2562/12* (2013.01); *A61B 2562/164* (2013.01)

(56) References Cited

OTHER PUBLICATIONS

Tsou et al., "Flexible Inkjet-Printed Multi-Ionic Sensor Tape for Biomedical Applications," 22nd International Conference onf Miniaturized Systems for Chemistry and Life Sciences, Nov. 11-15, 2018, pp. 908-911, 4 pages.

\* cited by examiner (a)

(b)

(a)

(b)

MINIATURIZED SENSING PROBE AND MANUFACTURING METHOD THEREOF

CROSS-REFERENCE TO RELATED APPLICATION

This application claims priority from Taiwan Patent Application No. 108114558, filed on Apr. 25, 2019, in the Taiwan Intellectual Property Office, the content of which is hereby incorporated by reference in its entirety for all purposes.

BACKGROUND OF THE INVENTION

1. Field of the Invention

The present invention relates to a miniaturized sensing probe and a manufacturing method thereof, more particular to a miniaturized sensing probe used to monitor biological values, such as temperatures, pH values, ions, and the like, in food and medical fields.

2. Description of the Related Art

In the medical field, it is often necessary to monitor various physiological values in real time to prevent patients' condition from suddenly deteriorating during surgery, treatment, or examination. Particularly, stopping the heart, lowering temperatures, and perfusing the myocardial vascular system are often required for conducting cardiac surgery due to the conventional procedure in the surgery process. This may lead to the occurrence of different sequelae after surgery, such as systemic non-specific inflammatory responses, deterioration of organ functions, changes in the endocrine system, abnormal metabolism and electrolytes, and the like. Nevertheless, medical staff nowadays may only monitor patients' post-surgical conditions by using monitoring methods, such as electrocardiograms, arterial pressure catheters, blood drawing, and the like, after patients have surgery. Methods for monitoring myocardial ischemia without the intervention in surgery have not been developed.

In addition, with an increase in the average age of citizens and changes in lifestyle and diet, a number of people with chronic diseases have been gradually growing, such as people with diabetes, high blood pressure, dyslipidemia, and the like. Hence, it is rather important to put great emphasis on the prevention of a peripheral vascular disease. The symptoms of the peripheral vascular disease includes muscle soreness caused by lower limb ischemia and powerless or intermittent lameness. When having a serious condition, patients may experience symptoms such as pains occurring during a rest or even skin ulcers. Generally, conventional methods for diagnosing a peripheral vascular disease nowadays are performed to approximately determine the location of vascular obstruction through palpation. For a more precise diagnosis, an angiography may be required to effectively determine the location of vascular obstruction. However, this examining method can merely identify the obstructed position of the blood vessel. If further determination of the necrosis of the limbs is required, it is necessary to rely on a wealth of experience of a surgeon for precise determination.

In addition, it is common to evaluate food items that may pose a threat to consumers' health through a scientific approach to reduce or avoid consumers' concerns in the aspect of food safety. Nonetheless, thousands of food items to be evaluated exist on the market. Even the use of sampling tests still requires tremendous manpower resources and expenses for inspection. Accordingly, a simple and fast detecting method is desperately required to detect the freshness of food without affecting the food or to detect whether potential safety concerns exist in the food.

In Hideaki Endo's paper (A needle-type optical enzyme sensor system for determining glucose levels in fish blood, Analytica Chimica Acta 573-574 (2006) 117-124), a needle-type enzyme sensor system was shown on FIG. 1 thereof. In this needle-type enzyme sensor system, an optic fiber probe was used, please see the content under the title of "2.2. Needle-type enzyme sensor and measurement" on right column of page 118. In FIG. 1(A) of Hideaki Endo's paper, it can be seen that many round-shaped holes 2 are disposed along the wall of the needle-type hollow container 1, and no partitions are disposed between the round-shaped holes 2.

SUMMARY OF THE INVENTION

Various kinds of sensors have been developed for applications on biomedical science; however, the size of conventional sensors usually have an area of a few square millimeters, resulting in the difficulty of realizing the implantation into tissues for a sensing process. Therefore, the present invention aims to provide a miniaturized sensing probe to enable the disposition of the miniaturized sensor on a probe substrate and the realization of combination with medical needles, which achieves effortless placing in tissues and food for performing a sensing procedure.

According to one aspect, the present invention provides a miniaturized sensing probe, including: a probe substrate including a probe part and a circuit connection part; a sensor disposed on the probe part and electrically connected to the circuit connection part; and a needle unit used to accommodate the probe part of the probe substrate; wherein the sensor performs sensing when placed into an analyte through the needle unit and transmits a sensing signal through the circuit connection part.

Preferably, the probe substrate is a silicon substrate or a flexible substrate.

Preferably, when the probe substrate is a silicon substrate, the sensor on the probe part includes at least one of a temperature sensor, a pH sensor, and an ionic sensor.

Preferably, when the probe substrate is a flexible substrate, the sensor disposed on the probe part includes at least one of a temperature sensor, a pH sensor, an ionic sensor, and a protein sensor.

Preferably, the protein sensed by the protein sensor is lactic acid or troponin.

Preferably, the flexible substrate is a biocompatible substrate or a biodegradable substrate.

Preferably, the needle unit has a caliber equal to or smaller than a caliber of a 23-gauge needle.

Preferably, the sensor further includes a reference electrode, and a polyvinyl chloride (PVC) layer containing chloride ion is disposed on the reference electrode.

Preferably, the sensor further includes a working electrode, and a polyvinyl chloride layer containing ions is disposed on the working electrode.

According to the another aspect, the present invention provides a manufacturing method for a miniaturized sensing probe, including the following steps: (a) forming a reference electrode on a portion of a probe substrate by an electroplating or inkjet process; (b) forming a working electrode on another portion of the probe substrate by a chemical vapor deposition or inkjet process; (c) forming a polyvinyl chloride layer on at least one of the reference electrode and the working electrode by an inkjet process; and (d) disposing the probe substrate in a needle unit.

According to the miniaturized sensing probe provided by the present invention, the present invention may have the following advantages:

(1) Through the protection of the medical needle, the miniaturized sensing probe of the present invention allows the probe substrate to be effortlessly placed into tissues without the use of other instrument or surgery. This is beneficial to a clinician performing an early diagnosis on a patient with a peripheral vascular disease. Moreover, under the condition that cardiac surgery is not intervened, the present invention may be applied to monitoring various biological values of muscles, thus instantly helping learn a patients' myocardial ischemic state for the prevention of various sequelae caused by surgery or for the decrease in the possibility of getting them.

(2) On the basis of the requirement, the miniaturized sensing probe of the present invention integrates several sensors, such as a temperature sensor, a pH sensor, an ionic sensor, or a protein sensor, on the probe substrate to assist medical staff in monitoring the instant condition of a patient.

(3) The miniaturized sensing probe of the present invention may also utilize a probe substrate with flexibility. Since the probe substrate may be rolled up into a cylindrical shape, the disposition area for sensors may increase. Further, the probe substrate in a cylindrical shape may be placed therein in the manner of sticking on the inner wall of the needle unit, and openings may be provided in the tube wall of the needle unit corresponding to the sensors, thus achieving an increase in the effectiveness of the sensing sensitivity and stability when disposing a plurality of measuring location points and a plurality of sensors.

DESCRIPTION OF THE PREFERRED EMBODIMENTS

Figure 1:
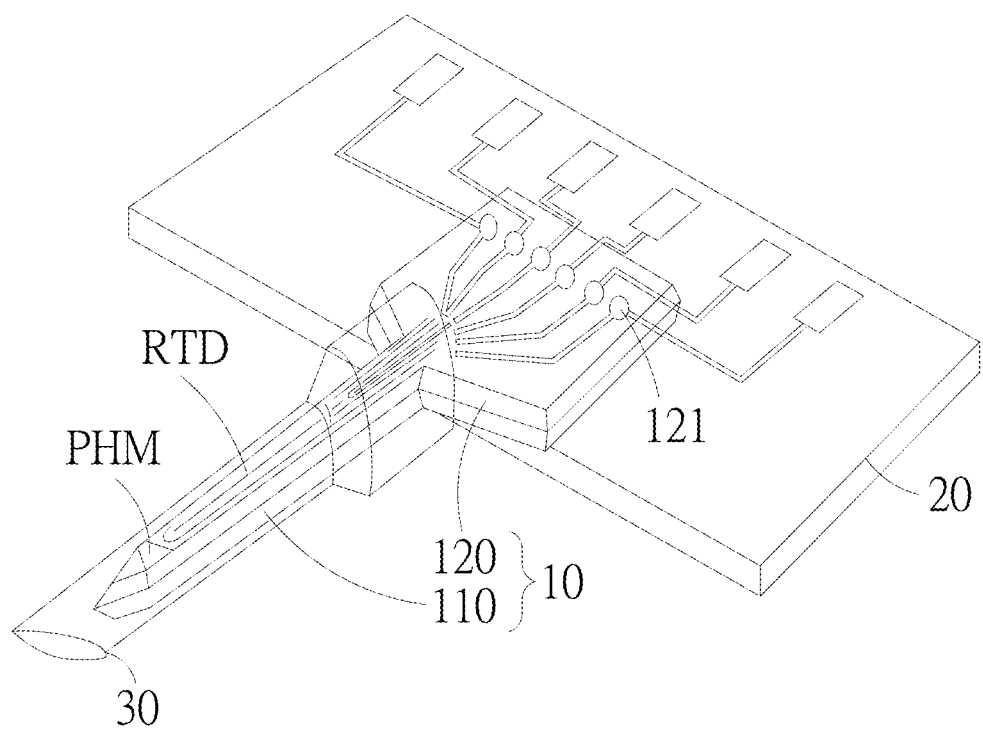
FIG. 1 depicts a schematic diagram of the miniaturized sensing probe according to the first embodiment of the present invention.

The advantages, features, and technical methods of the present invention are to be explained in detail with reference to the exemplary embodiments and the accompanying drawings for the purpose of being more easily to be understood. Moreover, the present invention may be realized in different forms, and should not be construed as being limited to the embodiments set forth herein. Conversely, for a person of ordinary skill in the art, the embodiments provided shall make the present invention convey the scope more thoroughly, comprehensively, and completely.

The various exemplary embodiments described herein with reference to the drawings are schematic illustrations of idealized exemplary embodiments and/or intermediate structures. Changes in shapes of patterns caused by manufacturing techniques and/or tolerances are expected; hence, the exemplary embodiments of the present invention should not be construed as being limited to specifically depicted shapes of regions, but should include changes in shapes caused by a manufacturing process, for instance. In addition, in the drawings, the sizes of the elements may be magnified for the convenience of explanation. The same element symbols may be denoted as the same elements throughout the specification and the drawings.

Figure 2:
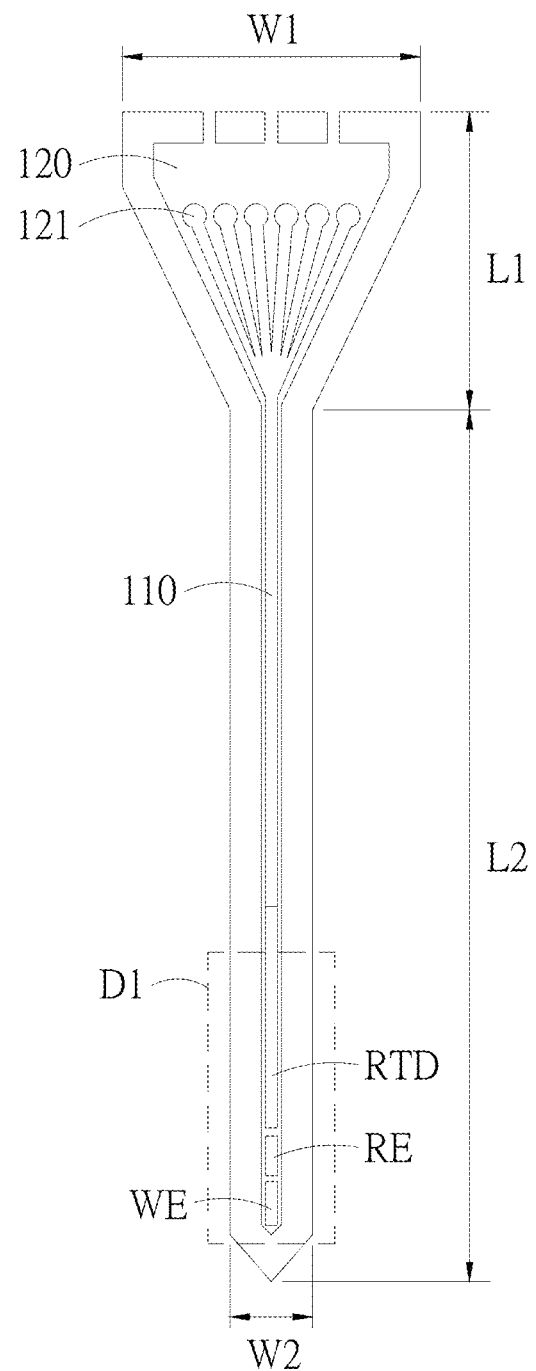
FIG. 2 depicts a planar graph of the probe substrate of the miniaturized sensing probe according to FIG. 1.
Figure 3:
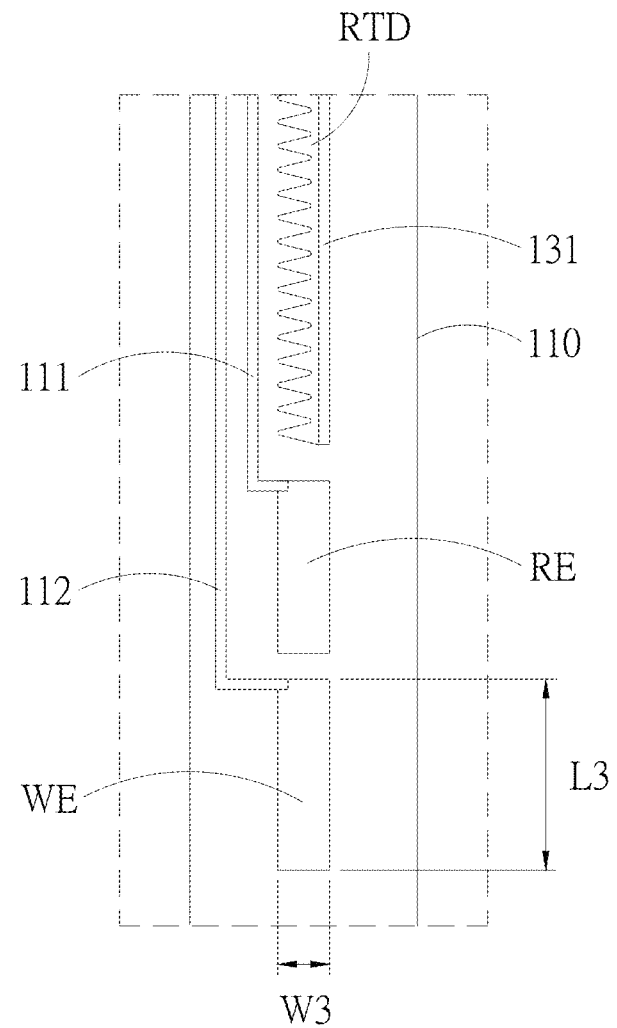
FIG. 3 depicts an enlarged diagram of D1 in FIG. 2.
Figure 4A:
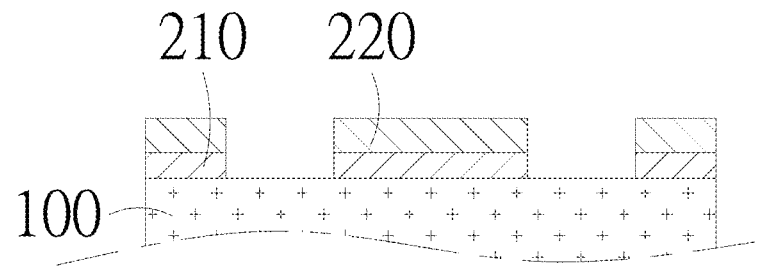
FIG. 4A to FIG. 4F depict processing sectional diagrams for manufacturing the miniaturized sensing probe of the present invention.
Figure 4B:
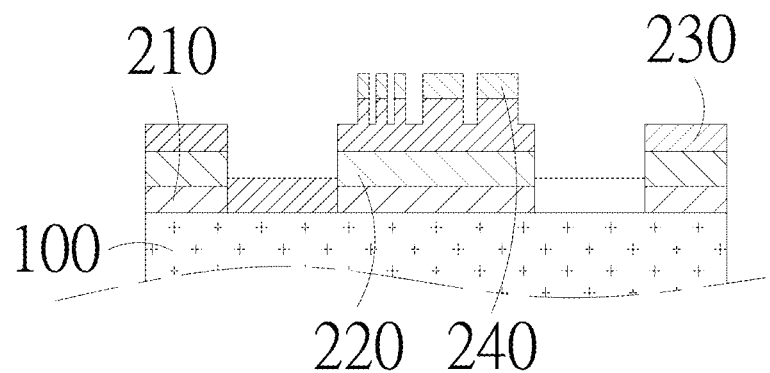
Figure 4C:
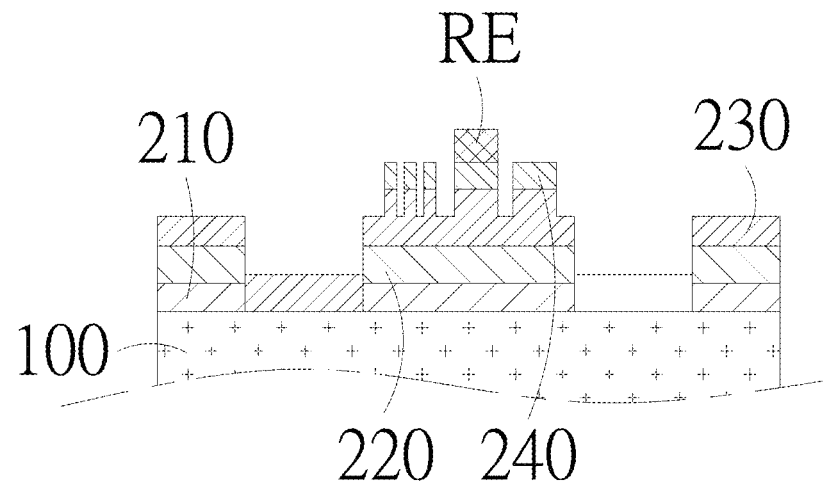
Figure 4D:
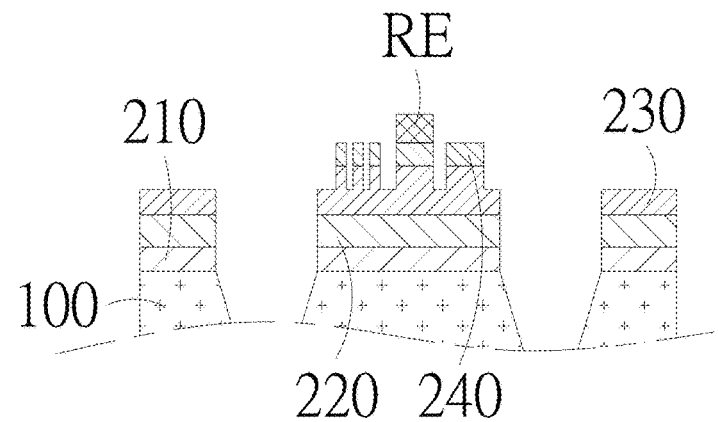
Figure 4E:
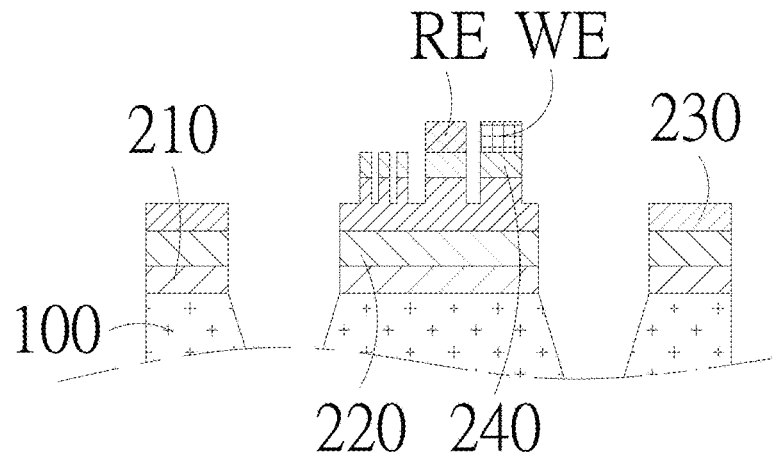
Figure 4F:
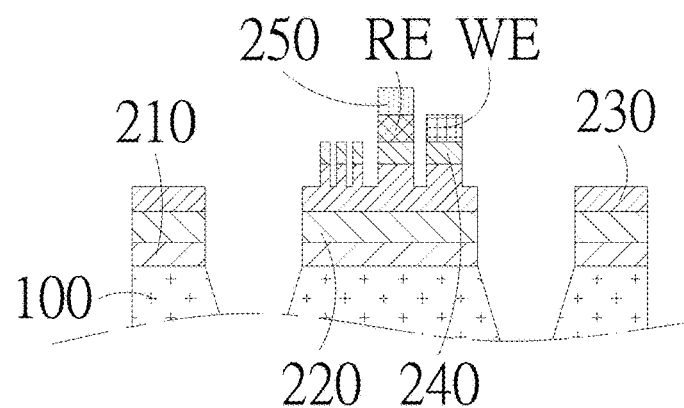

Please refer to FIG. 1 to FIG. 3; FIG. 1 depicts a schematic diagram of the miniaturized sensing probe according to the first embodiment of the present invention; FIG. 2 depicts a planar graph of the probe substrate of the miniaturized sensing probe according to FIG. 1; FIG. 3 depicts an enlarged diagram of a portion of the sensor in FIG. 1. According to a first embodiment, the present invention provides a miniaturized sensing probe, including a probe substrate 10 including a probe part 110 with a narrower width and a circuit connection 120 provided with connection points 121 with a broader width; a temperature sensor RTD and a pH sensor PHM disposed on the probe part 110 and electrically connected to the circuit connection part, whereas the type of the setting of the sensor is only exemplary, meaning that a user may dispose a variety of other types of sensors such as a sodium ionic sensor, a potassium ionic sensor, or a calcium ionic sensor according to requirements; a circuit substrate 20 electrically connected to the circuit connection part 120 of the probe substrate 10 so as to transmit the signal sensed by each sensor to the outside for analysis; and a needle unit 30 used to accommodate the probe part 110 of the probe substrate 10. In the present embodiment, the thickness of the probe substrate 10 may be about 200 μm to 400 μm, preferably being a silicon substrate at the thickness 250 μm or 300 μm; wherein the width W1 of the circuit connection part 120 may be 2 mm to 6 mm, preferably the width W1 being about 4.3 mm, and the length L1 thereof may be about 2 mm to 6 mm, preferably the length L1 being about 4.75 mm; the width W2 of the probe part 110 may be about 300 μm to 700 μm, preferably the width W2 being about 400 μm, and the length L2 thereof may be about 13 mm to 25 mm, preferably the length L2 being about 15 mm. In addition, the edge of the probe part 110 may have a characteristic angle of 54 degrees, but the present invention is not limited thereto. That is, the user may dispose the edge of the probe part 110 as an edge easily being placed into the needle unit 30 based on requirements. Therefore, for the miniaturized sensing probe of the present invention, the probe part 110 may be evenly disposed in the needle unit 30 because of having a specific size and angle as mentioned above, thus transmitting the signal to the outside through the circuit connection part 120 and the circuit substrate 20. It is worth mentioning that the needle unit 10 used in the present invention is a medical steel needle with the inner diameter equal to or smaller than that of the 23-gauge needle, preferably the 18 to 22-gauge needles, more preferably the 20 and 21-gauge needles, such as the needle with an inner diameter being 0.838, 0.686, 0.603, 0.514, 0.413, or 0.337 mm. However, the present invention is not limited thereto; that is, according to the purpose and requirements for use, a needle with a suitable inner diameter may be adopted. For instance, the 17-gauge needle may also be used for food detection.

Please further refer to FIG. 2 and FIG. 3. The pH sensor PHM is disposed on one end of the probe part 110 away from the circuit connection part 120, and the pH sensor PHM may include a reference electrode RE and a working electrode WE. The signals sensed by the reference electrode RE and the working electrode WE may be transmitted to the connection points 121 on the circuit connection part 120 via the conducting wires 111, 121 respectively; the signal is further transmitted to the circuit substrate 20 via the connection points 121. Wherein, the material of the reference electrode RE may be silver (Ag) and/or silver chloride (AgCl); the material of the electrode WE may be cerium oxide ($IrO_x$) having excellent biocompatibility, high sensitivity, and high stability. However, the present invention is not limited thereto; that is the reference electrode RE and the working electrode WE may be formed by selecting other suitable metal materials. In addition, a polyvinyl chloride (PVC) layer containing chloride ions may be additionally formed on the reference electrode RE. The width W3 of the reference electrode RE or the working electrode WE may be 100 to 200 preferably the width W3 being 120 to 150 and the length L3 thereof may be 200 to 850 preferably the length L3 being 240 to 750 In the present embodiment, the size of the reference electrode RE and the working electrode WE is 150×750 μm². The pH sensor PHM of the present invention may be based on the Nernst equation, as shown in Formula (1) as follows:

$$E = E^0 - 2.303 \frac{RT}{F} \text{pH} = E^0 - 0.05916 \, \text{pH} \tag{1}$$

Wherein, F represents a Faraday constant, where the value is 96500 C/mole; R represents a gas constant, where the value is 8.314 J/mole·K; $E^0$ is the standard potential of 577 mV of silver chloride. According to Formula (1), it is known that the acid-base sensing theoretical value is about −59 mV/pH at room temperature of 25° C.

In the present embodiment, the temperature sensor RTD on the probe part 110 may be a resistive temperature sensor, and is disposed adjacent to the pH sensor PHM, but the present invention is not limited hereto. That is, the temperature sensor RTD or the pH sensor PHM may be respectively disposed at a required position along a length direction of the probe part 110 according to the depth position actually required for sensing. According to the fundamental principle of the temperature sensor RTD of the present invention, the metal resistance changes linearly with the changes in temperature. Thus, according to Formula (2) as follows, the resistance value is converted by measuring the voltage at the two-end points in the middle to be further converted into temperature with external two ends of the conducting wires 131 conducting current (current 5.00×10⁻⁴ A) through the method of using a four-point probe to measure resistance.

$$TCR(\alpha) = \frac{1}{R} \frac{\partial R}{\partial T} \tag{2}$$

Wherein, TCR is the temperature coefficient, R is the resistance at the reference temperature, ∂R is the resistance change at different temperatures, and ∂T is the temperature change.

The resistance wire used in the present invention is a copper metal conducting wire of about 25Ω. Owing to the advantages of copper, such as the excellent temperature coefficient (TCR ~4.27×10⁻³/° C.), low costs, wide sensing ranges, high accuracy, fast reaction time, high stability, easy electroplating, and being suitable for silicon manufacturing process, copper is selected as the conducting material and a gold layer after replacing the nickel gold is used for protecting the copper from being oxidized. Based on the width of the probe part 110, the copper conducting wire has a line width of about 8 to 12 μm, preferably 10 μm; the total length of the resistance wire coiled in a wiggle shape is about 7000 μm.

Please refer to FIG. 4A to FIG. 4F, which depict processing sectional diagrams for manufacturing the miniaturized sensing probe of the present invention. The steps of the manufacturing process of the miniaturized sensing probe of the present invention include: using RIE to perform the openings of the front mask layer to define the pattern of the probe substrate 10 (referring to FIG. 4A) by the low-pressure chemical vapor deposition (LPCVD) after the oxide layer 210 (thickness: 500 nm) and the nitride layer 220 (thickness: 800 nm) are respectively deposited on the silicon substrate 100 with a thickness of 250 μm; depositing the seed layer 230 containing titanium (Ti) and/or copper (Cu) having a thickness of 30 nm to 120 nm and the coating layer used to define the region of the conducting wire and the external electrical connection points (not shown) on the nitride layer 220, and electroplating a 1 μm copper layer (Cu) without electroplating 0.1 μm to 0.4 μm nickel (Ni) and/or gold (Au) as a protective layer 240 to form the temperature sensor RTD (referring to FIG. 4B); electroplating a material containing silver and/or silver chloride on the protective layer 240 to form the reference electrode RE having a thickness of about 1.5 μm (referring to FIG. 4C); using KOH to perform etching to form the pattern of the probe substrate (referring to FIG. 4D); depositing and pattering a material containing cerium oxide (Ir) to form the working electrode WE (referring to FIG. 4E); forming the PVC layer 250 on the reference electrode RE by inkjet printing, and soaking it in 0.01 M of KCl for 3 days to form a pH sensor PHM (referring to FIG. 4F); and electrically connecting the probe substrate 10 on which the sensor is formed to the circuit substrate 20, disposing the probe part 110 of the probe substrate 10 in the needle unit 30, and fixing the circuit connection part 120 and the circuit substrate 20 together by an adhesive (glue) to obtain a miniaturized sensing probe.

Figure 5:
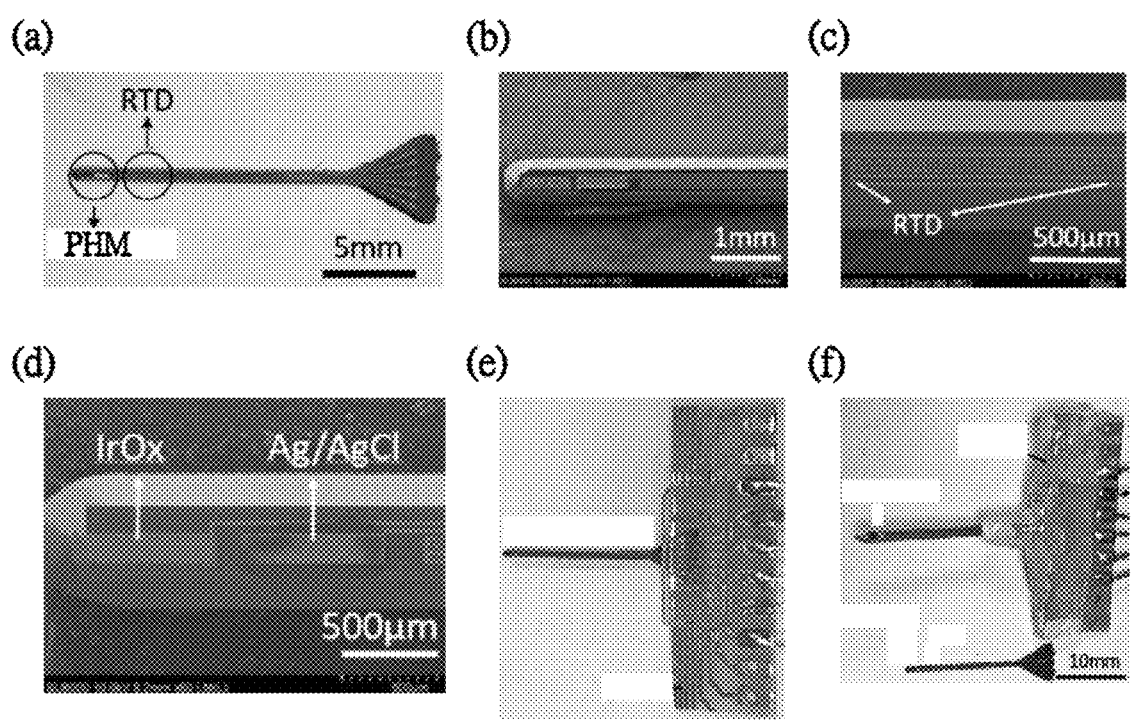
FIG. 5 shows an image of the miniaturized sensing probe prepared according to the first manufacturing process of the present invention, wherein (a) depicts an image of the probe substrate according to the first embodiment of the present invention; (b) depicts an electron microscopic image of the probe part of the probe substrate; (c) depicts an electron microscopic image of the pH sensor formed on the probe part; (d) depicts an electron microscopic image of the temperature sensor formed on the probe part; (e) depicts an image of the combination of the probe substrate and the circuit substrate; and (f) depicts an image of the miniaturized sensing probe of the present invention.
Figure 6:
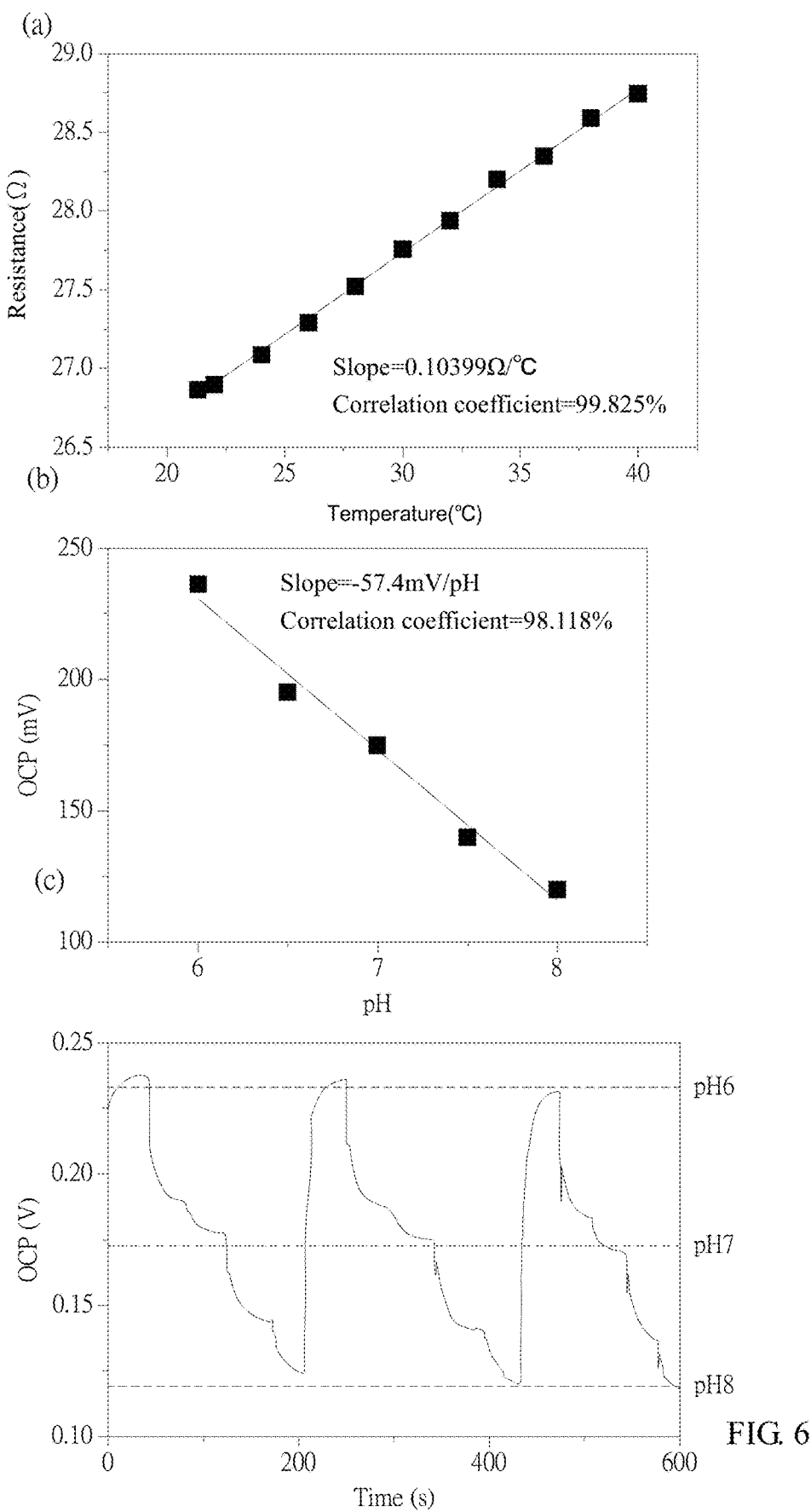
FIG. 6 depicts measurement results of using the probe substrate according to the first embodiment of the present invention to measure temperatures and pH values, wherein (a) depicts a result of the temperature sensor sensing temperatures; (b) depicts a result of the pH sensor sensing pH values; (c) depicts a result of recoverability of the pH sensor.

Please refer to FIG. 5 and FIG. 6; FIG. 5 shows an image of the miniaturized sensing probe prepared according to the first manufacturing process of the present invention; FIG. 6 depicts measurement results of using the probe substrate according to the first embodiment of the present invention to measure temperatures and pH values. According to the first embodiment of the present invention, the measurement of temperature and pH values is practically performed on the probe substrate prepared by the aforementioned manufacturing process to confirm the sensitivity and stability. The resistance change of the temperature sensor of the present invention is measured by the Keysight B2902A for the four-point probe measurement. $5 \times 10^{-4}$ A of current is applied to measure the voltage value for conversion into a resistance value, and the calibration of the temperature measurement is performed by placing the temperature sensor on the heating plate for water heating. A point is measured every 2° C. in a range from 20° C. to 40° C. The results of FIG. 6(a) shows that the temperature sensor of the present invention may achieve a linear sensitivity of about 0.105Ω/° C. and a correlation coefficient of 99.825%.

Then, the open circuit potential (OCP) corresponding to a pH value is further detected with the use of the probe substrate of the present invention. The pH value is measured by using the OCP sensed by the probe substrate of the present invention, which is performed by Jiehan-5600 Electrochemical Workstation. Considering that the pH value of healthy human blood and tissue fluid is at about 7.4, the OCP is measured in the phosphate buffer solutions respectively at pH 6, pH 6.5, pH 7, pH 7.5, and pH 8. According to the results of FIG. 6(b), the pH sensor of the present invention may achieve a linear sensitivity of −57.4 mV/pH and a correlation coefficient of 98.118% at room temperature. Furthermore, according to the results of FIG. 6(c), three cycles are measured at pH 6, pH 6.5, pH 7, pH 7.5, and pH 8 using the pH sensor of the present invention. The result shows that each pH value is accurately measured under the three cycles, meaning that the pH sensor of the present invention has excellent recoverability.

Figure 7:
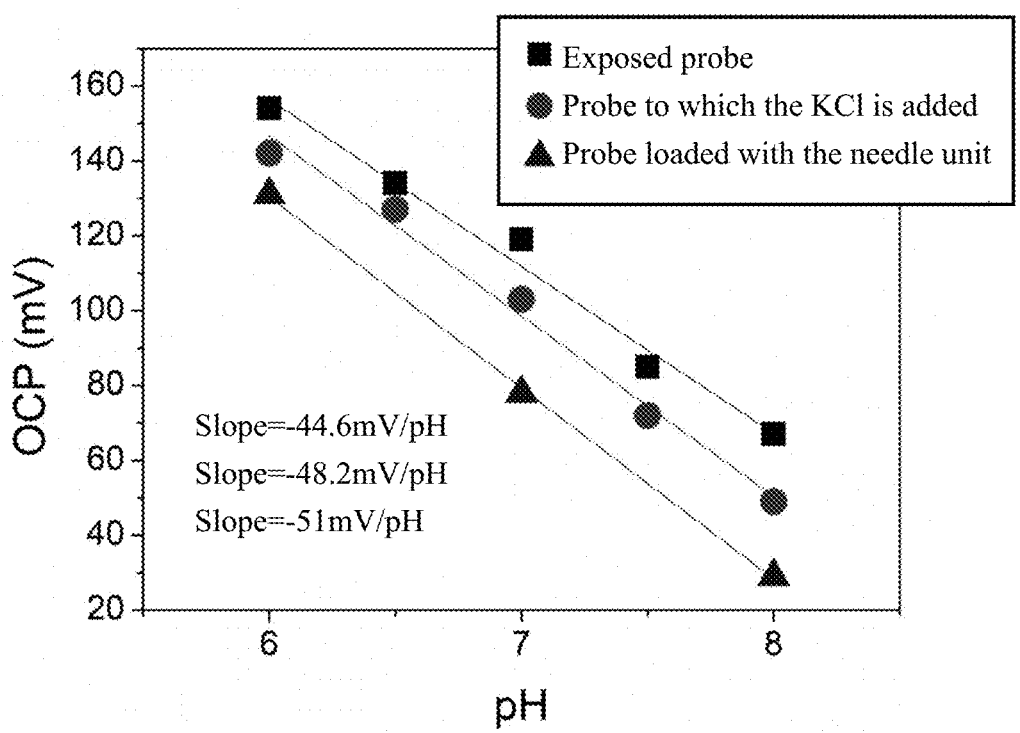
FIG. 7 depicts a graph of the impact of loading the needle unit and adding 0.1 M KCl to the pH sensor on pH values.

Please refer to FIG. 7 which depicts a graph of the impact of loading the medical steel needle and adding 0.1 M KCl to the pH sensor on pH values. The probe substrate 10 of the present invention does not seriously affect the pH sensor PHM after being loaded into the needle unit 30; thus, the probe may not be short-circuited. According to the results of FIG. 7, it is shown that the linear sensitivity of the probe (the ● of FIG. 7) to which the KCl is added and the probe having a reference electrode RE of the PVC layer 250 and loaded with the needle unit 30 (the ▲ of FIG. 7) are both close to the theoretical value, −59 mV/pH. The reason may account for the fact that general reference electrodes on the market need to be stored in 3 M of the KCl solution. However, the exposed probe with the reference electrode placed in the air for a period of time without a PVC layer thereon (■ of FIG. 7) has a linear sensitivity only up to −44.6 mV/pH. This shows that the Cl ions in the solution may be slightly stabilized due to the reference electrode RE after 0.1 M of the KCl is added to the buffer solution. On the other hand, the value with the PVC layer 250 containing chloride ion covering the reference electrode RE may be closer to the theoretical value, meaning the importance of the reference electrode RE covering the PVC layer 250 containing Cl ions.

Figure 8:
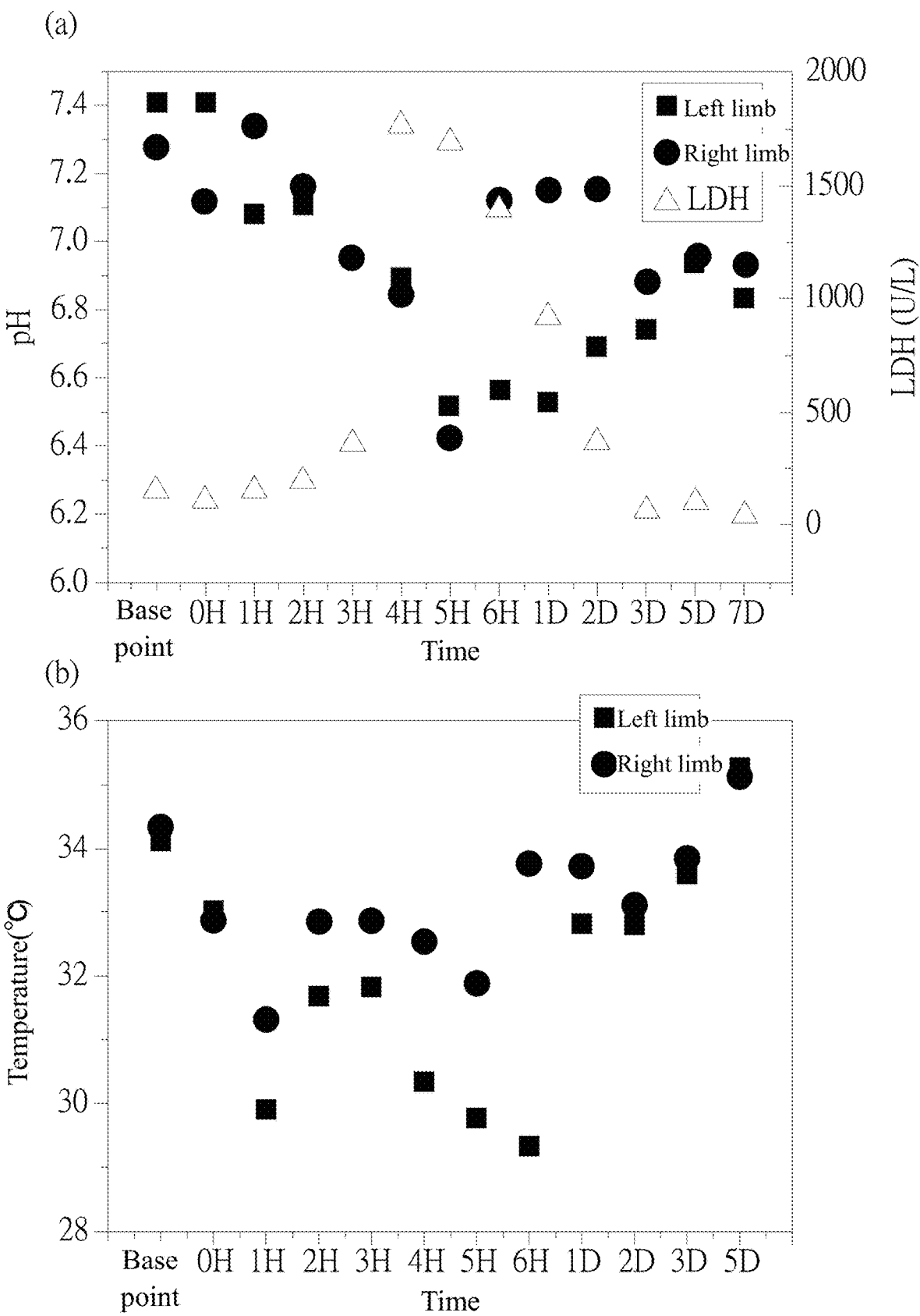
FIG. 8 depicts graphs of the miniaturized sensing probe of the present invention applied to monitoring the muscle of the lower limb of a rabbit, wherein (a) depicts a result of monitoring the pH value and LDH concentration in blood regarding the muscle of the lower limb of a rabbit; and (b) depicts a result of monitoring the temperature of the muscle of the lower limb of a rabbit.

Please further refer to FIG. 8. Since the mechanism and the performance of muscular necrosis caused by peripheral arterial vascular obstruction are similar to those of a myocardium, the miniaturized sensing probe of the present invention is further applied to monitoring the lower limb muscle of a living animal. As shown in FIG. 8(a), the experimental method is that the blood vessels of the left limb of the rabbit are ligated to make them become necrosis; compared to the unligated blood vessels of the right limb, changes in the pH value and temperature are respectively detected through the use of the miniaturized sensing probe; the obtained pH value is then compared to the value of lactic dehydrogenase (LDH) of the blood vessel to find the relevance in organic muscular necrosis. Since the LDH is often stored in organs, such as a heart, a liver, muscle, when muscular necrosis occurs in a body, a large amount of LDH existed in muscle cells is released to the blood, which shows that the concentration of LDH in the blood increases with the degree of muscular necrosis. Similarly, after the muscular ischemic necrosis, a large amount of acidic substances such as phosphate and sulfate is also released into the blood, leading to an decrease of the pH value in the blood along with the degree of muscular necrosis. According to the results of FIG. 8(b), the pH value measured from the artery of the ligated left limb (■ in FIG. 8(b)) is significantly smaller than the pH value measure from the artery of the unligated right limb (● in FIG. 8(b)) in the control group at the time point of 6 hours to 2 days. This shows that the pH sensor PHM of the present invention indeed has excellent sensitivity for sensing the pH value at different parts of a body, and the change in the pH value of the artery of the left limb has relevance to the change in the LDH value in the blood (Δ in FIG. 8(b)). Furthermore, according to the results of FIG. 8(c), the muscle temperature measured from the artery of the left limb (■ in FIG. 8(c)) is closer to the ambient temperature and significantly lower than the temperature of the artery of the right limb (● in FIG. 8(c)). This shows that poor blood circulation in the left limb of the rabbit results in a decrease in the temperature of the left limb.

Only puncturing muscle with the probe substrate 10 may easily cause the probe part 110 to break, failing to perform penetration in the muscle. As a result, the present invention combines the probe substrate 10 having the pH sensor PHM and the temperature sensor RTD with the needle unit 30. Moreover, it is showed that the changes in the pH value and temperature in muscle tissue fluid have a similar trend compared to lactic dehydrogenase (LDH) through instantly monitoring the pH value and temperature of the lower limbs of the rabbit having muscular necrosis due to ligating the blood vessels according to the animal experiment. Accordingly, the miniaturized sensing probe of the present invention may be effectively applied to monitoring muscular ischemia, further decreasing the risk of muscular necrosis.

Figure 9:
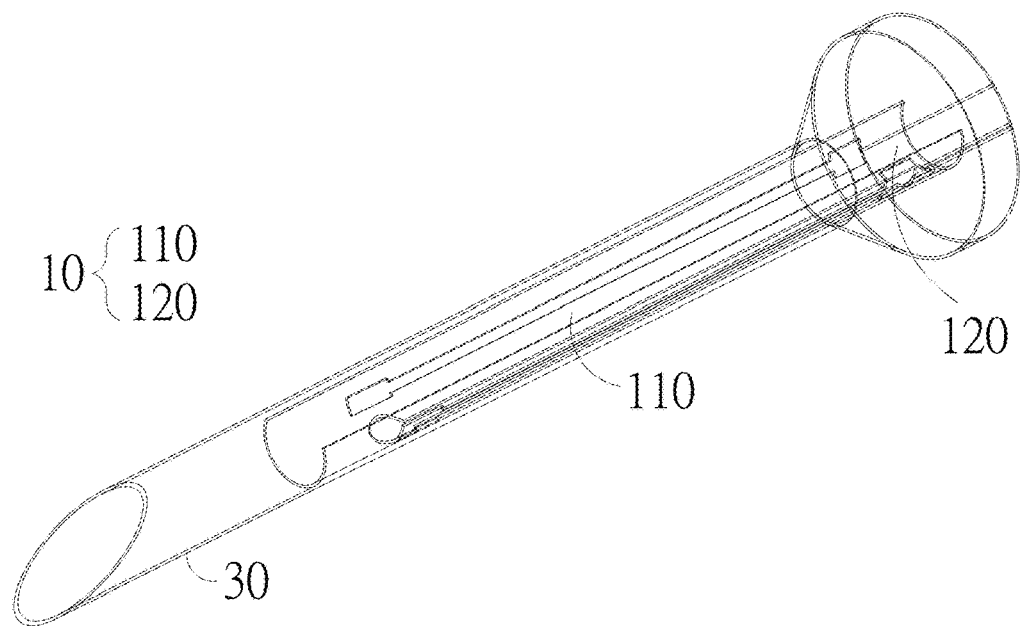
FIG. 9 depicts a schematic diagram of the miniaturized sensing probe according to the second embodiment of the present invention.
Figure 10:
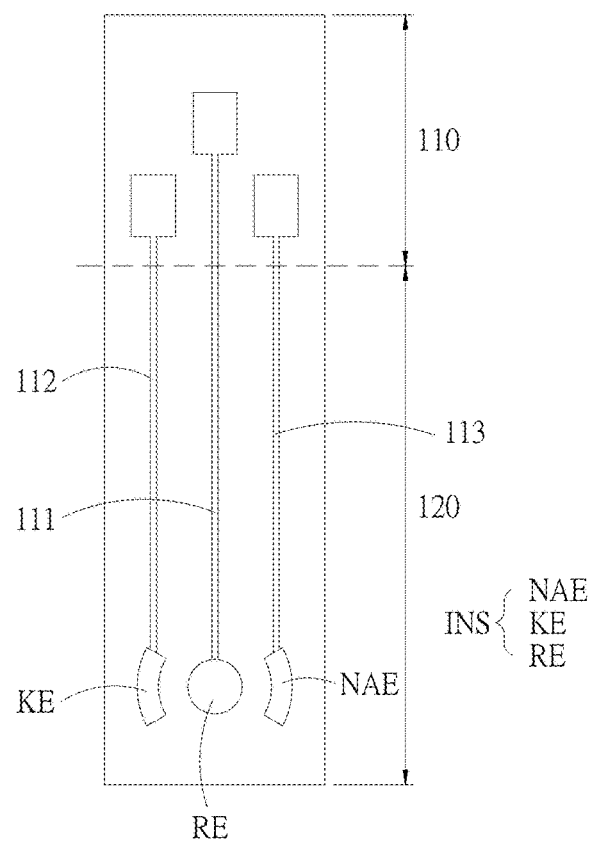
FIG. 10 depicts a planar graph of the probe substrate of the miniaturized sensing probe according to FIG. 9.

Please refer to FIG. 9 and FIG. 10; FIG. 9 depicts a schematic diagram of the miniaturized sensing probe according to a second embodiment of the present invention; FIG. 10 depicts a planar graph of the probe substrate of the miniaturized sensing probe according to FIG. 9. The main difference between the second embodiment and the aforementioned embodiment lies in the fact that the probe substrate 10 is a flexible substrate. According to the second embodiment, the present invention provides a miniaturized sensing probe, including: a probe substrate 110 including a probe part 110 and a circuit connection part 120; an ionic sensor INS disposed on the probe part 110 and electrically connected to the circuit connection part 120; and a needle unit 30 used to accommodate the probe part 110 of the probe substrate 10; wherein the circuit connection part 120 may be connected to an external circuit to transmit a sensing signal for analysis. In the present embodiment, the probe substrate 10 is a biodegradable flexible substrate, and the probe substrate 10 and the needle unit 30 are separable. Therefore, after the miniaturized sensing probe of the present embodiment is placed in the body by the needle unit 30, the needle unit 30 may be withdrawn to leave the probe substrate 10 in the tissue. In doing so, after the completion of the detection, the probe substrate 10 may be directly degraded in the body without the need for removal. In addition, the ionic sensor INS of the present embodiment may be disposed at one end of the probe part 110 away from the circuit connection part 120, and include a sodium ionic electrode NAE, a potassium ionic electrode KE, and a reference electrode RE disposed between the sodium ionic electrode NAE and the potassium ionic electrode KE. Moreover, the reference electrode RE, the potassium ionic electrode KE, and the sodium ionic electrode NAE may respectively transmit the sensed signals to the outside for analysis through the conducting wires 111, 112, and 113 extending to the connection points 121 of the circuit connection part 120.

The miniaturized sensing probe of the present embodiment may be manufactured by using the manufacturing process of CPLoP (Combined Process of Lift-off and Printing). The steps of the manufacturing process are presented as follows: (a) patterning a negative photo-resistance SU-8 on the probe substrate 10 to define the shapes of the conducting wires 111, 112, and 113; (b) performing an inkjet process by using a material containing, for instance, silver (Ag) to form conducting wires 111, 112, and 113; (c) removing the negative photo-resistance SU-8; patterning another negative photo-resistance SU-8 to define the working electrode and the reference electrode RE; (d) printing and chlorinating by using a material containing Ag to form an Ag/AgCl layer, and printing the solution containing chloride ion ($Cl^-$) as shown in Table 1 on the Ag/AgCl layer to form a polyvinyl chloride (PVC) layer containing chloride ion, thus completing the manufacture of the reference electrode RE; (e) performing inkjet printing by using poly(3,4-ethylenedioxythiophene) polystyrene sulfonate (PEDOT:PSS) to form a working electrode having a size of, for instance, 120×240 $\mu m^2$; and (f) separately printing the solution containing potassium and sodium as shown in Table 1 on the working electrode to form a sodium ionic electrode NAE and a potassium ionic electrode KE.

TABLE 1

| Type of PVC layer | Matrix | Ionophore | Lipophilic additive | Plasticizer | Solution |
|---|---|---|---|---|---|
| Sodium | PVC[a]/ 33 mg | Sodium ionophore X/ 1 mg | Na-TFPB[b]/ 0.5 mg | DOS[c]/ 65.5 mg | Cyclohexanone/ 3.5 g |
| Potassium | PVC/ 33 mg | Valinomycin/ 2 mg | NaTPB[d]/ 0.5 mg | DOS/ 64.5 mg | Cyclohexanone/ 3.5 g |
| Chloride | PVC/ 33 mg | Ionic liquid[e]/ 2 mg | | DOS/ 65 mg | Cyclohexanone/ 3.5 g |

Figure 11:
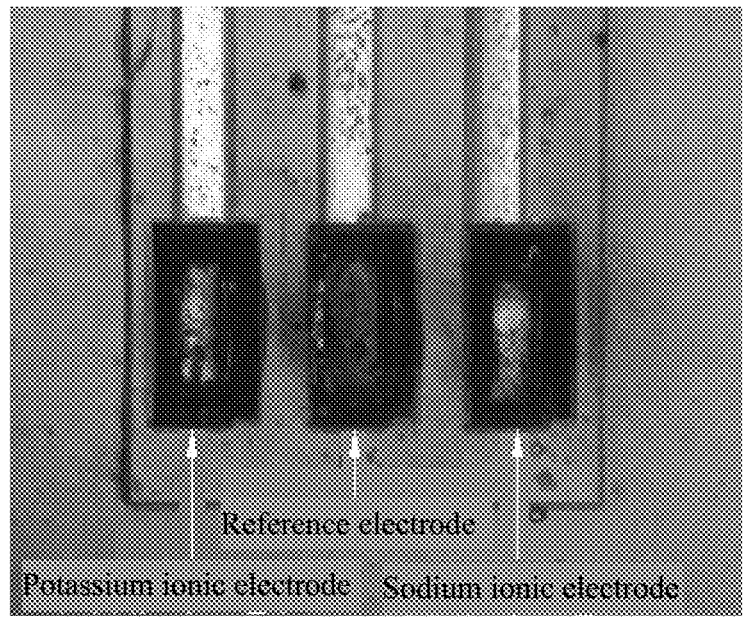
FIG. 11 shows an image of the miniaturized sensing probe prepared according to the second manufacturing process of the present invention, wherein (a) depicts an image of the probe part of the probe substrate according to the second embodiment of the present invention; and (b) depicts an electron microscopic sectional image of each electrode on the probe part.
Figure 11:
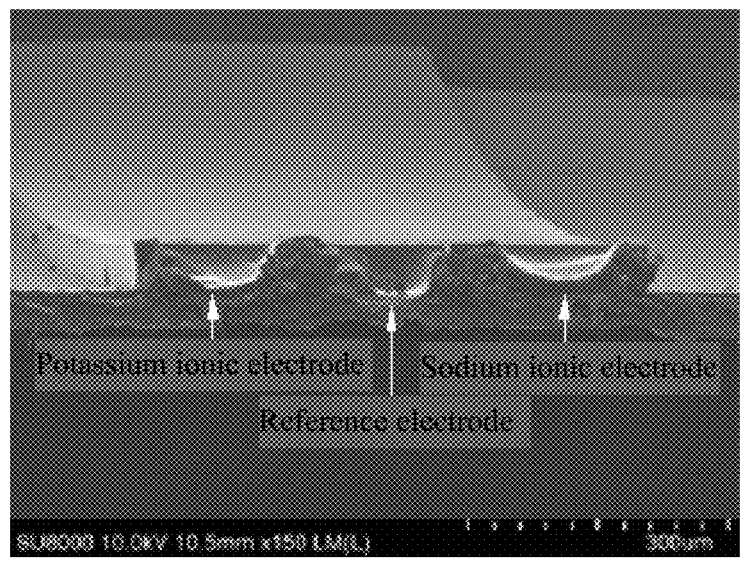

[a]poly(vinyl chloride)
[b]sodium tetrakis[3,5-bis(trifluoromethyl)phenyl] borate)
[c]bis(2-ethylhexyl) sebacate
[d]sodium tetraphenylborate
[e]1-dodecyl-3-methylimidazolium chloride As shown in FIG. 11 which shows images of the miniaturized sensing probe prepared according to the second manufacturing process of the present invention. FIG. 11 shows the reference electrode RE formed of a material containing Ag/AgCl being disposed at a middle position of the end of the probe part 110, and the sodium ionic electrode NAE and the potassium ionic electrode KE respectively adjacent to the reference electrode RE. This indicates that a small-sized electrode capable of scaling may be formed on the probe substrate 10 without additionally patterning the mask by using the manufacturing process of the present invention as mentioned above.

Figure 12A:
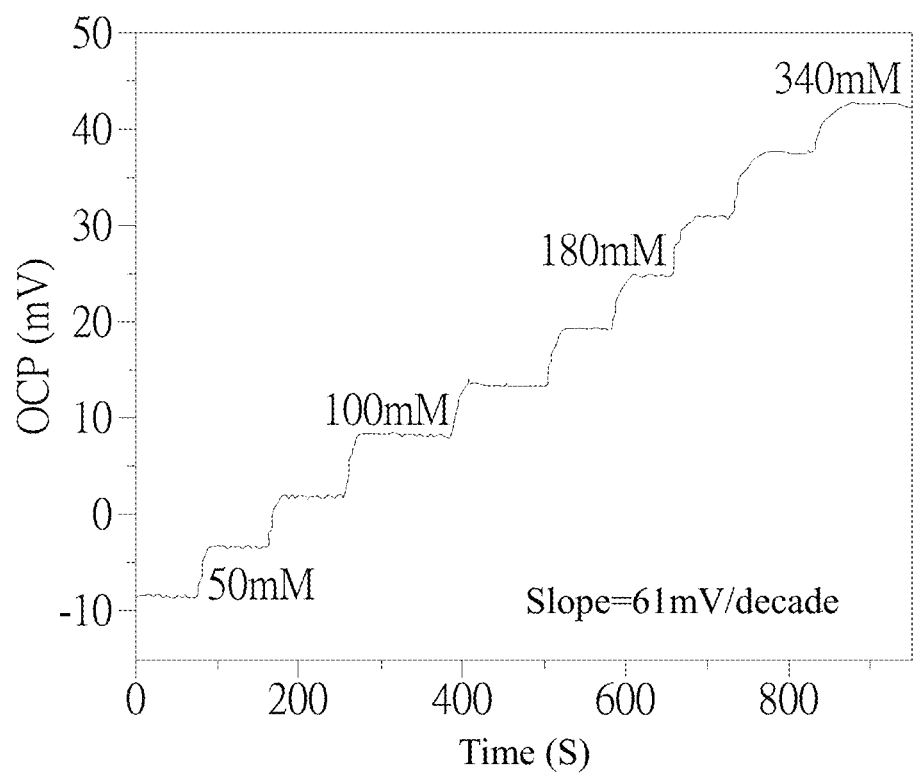
FIGS. 12A to 12F depict comparative results of the $Na^+$ and $K^+$ ion concentrations in the buffer solutions of different ion concentrations using the probe substrate according to the second embodiment of the present invention and the commercial electrode.
Figure 12B:
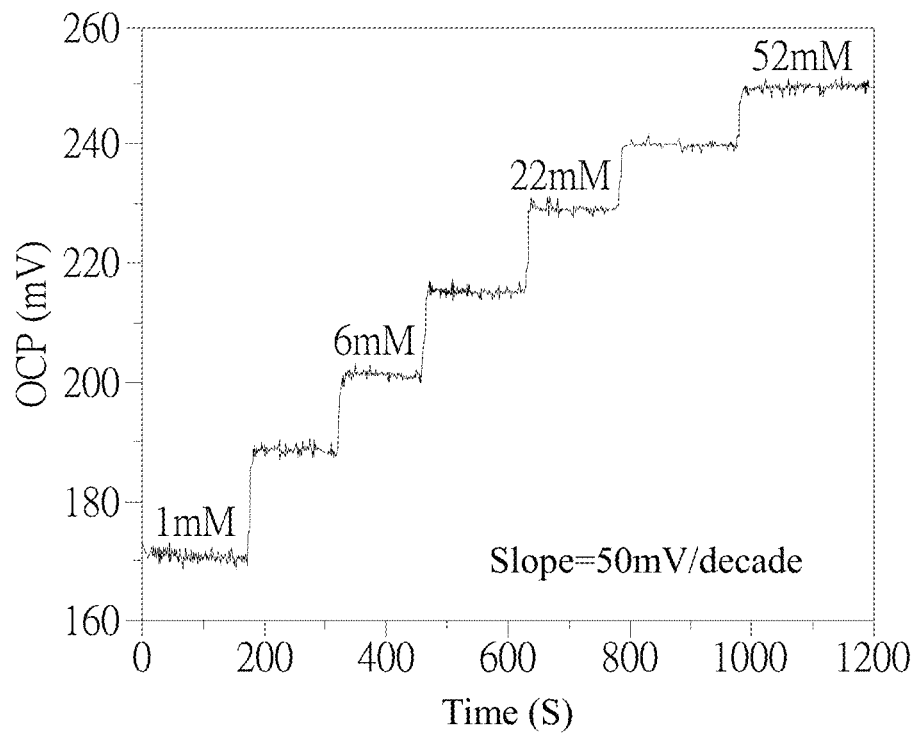
Figure 12C:
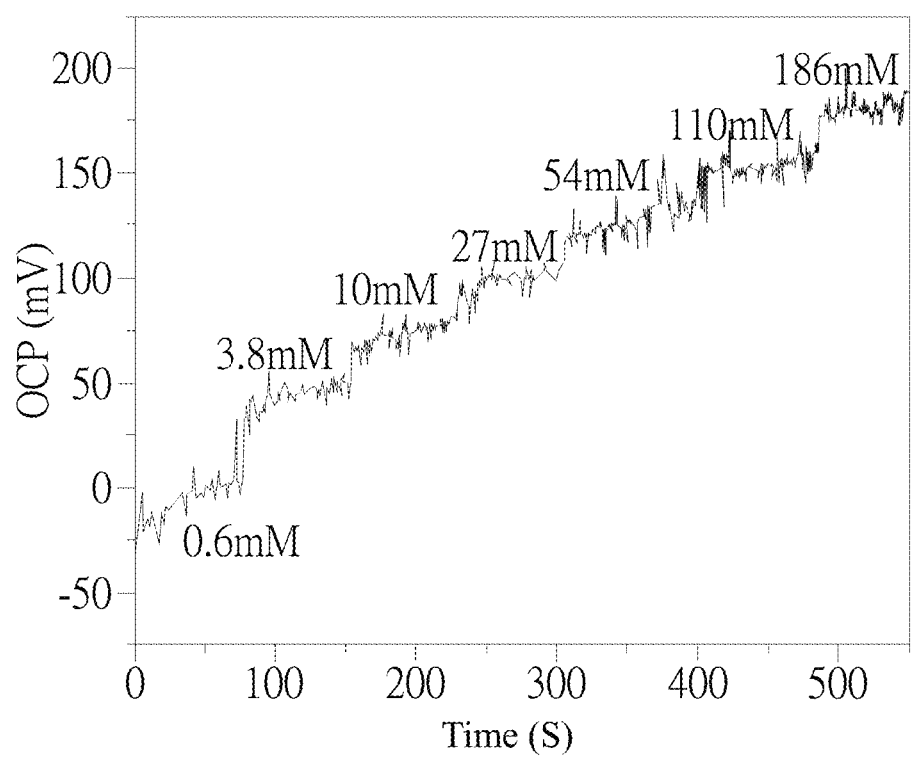
Figure 12D:
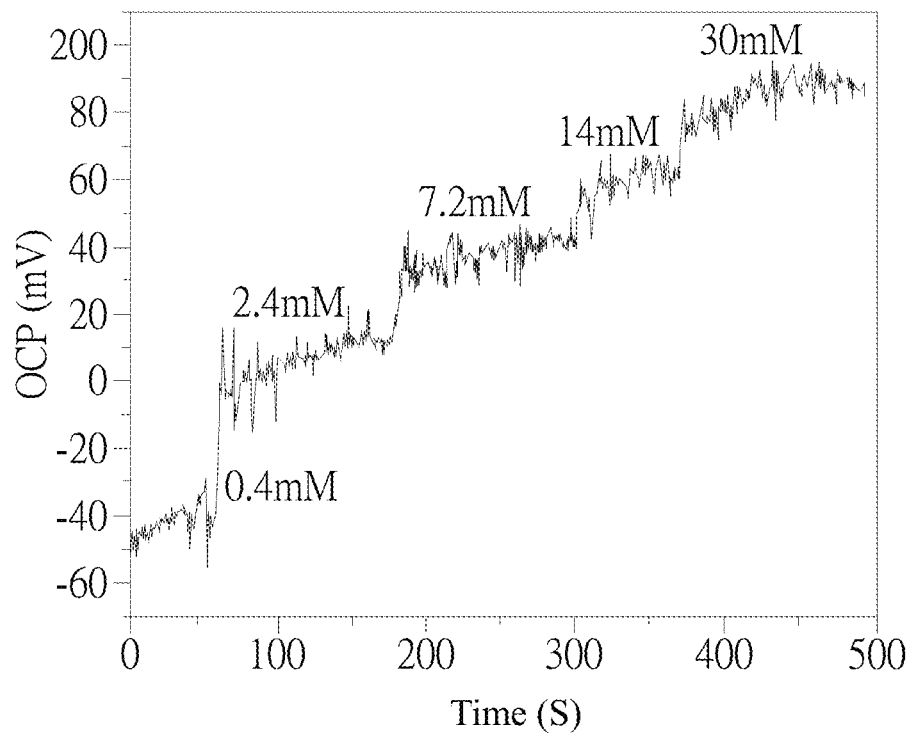
Figure 12E:
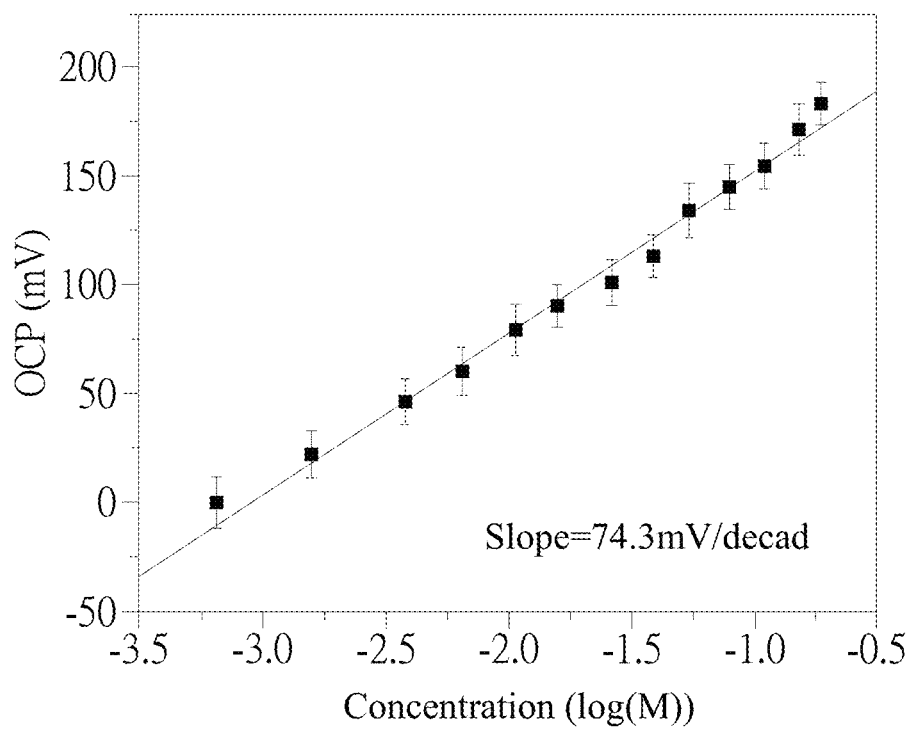
Figure 12F:
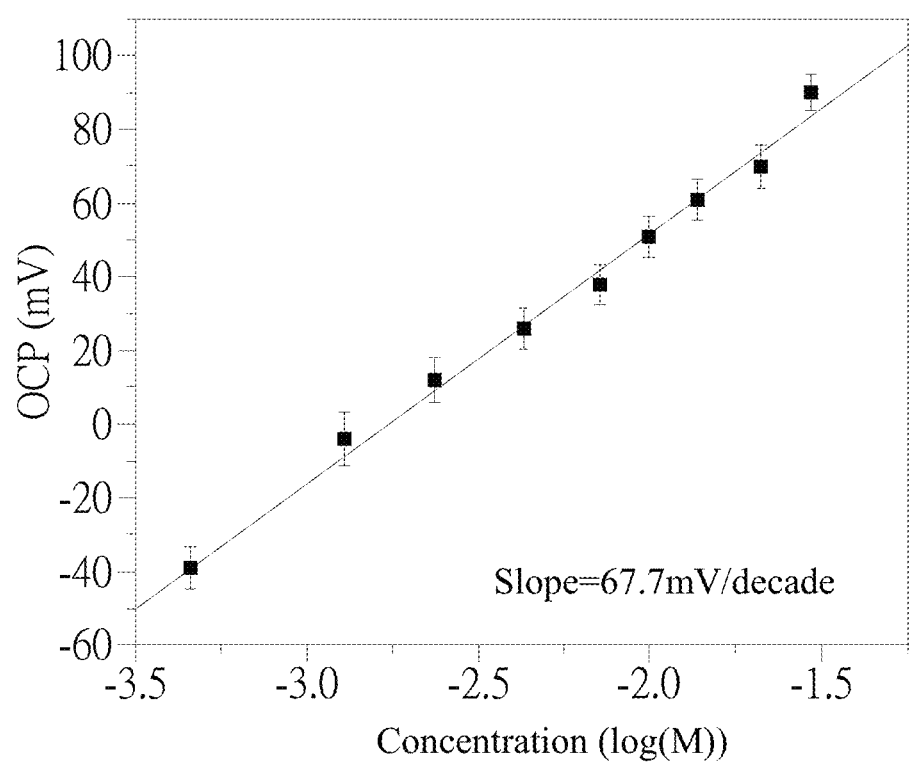

Please refer to FIG. 12A to FIG. 12F which depict comparative results of the $Na^+$ and $K^+$ ion concentrations in the buffer solutions of different ion concentrations using the probe substrate according to the second embodiment of the present invention and the commercial electrode. Specifically, FIG. 12A to FIG. 12B respectively are the results of the sodium ions and potassium ions of OCP measured at different ion concentrations for a sodium ionic electrode and a potassium ionic electrode with respect to the commercial electrode of Van London 5771423; FIG. 12C and FIG. 12D respectively are the results of the sodium ions and potassium ions of OCP measured at different ion concentrations for a sodium ionic electrode and a potassium ionic electrode with respect to the reference electrode combined with the Ag/AgCl and Pt counter electrode; and FIG. 12E and FIG. 12F respectively are the sensitivity measurements of the fully printed sodium ionic electrode and potassium ionic electrode, wherein the linear sensitivity of the sodium ionic electrode is 74 mV/decade and the sensing range is 0.6 to 200 mM, and the linear sensitivity of the potassium ionic electrode is 67 mV/decade and the sensing range is 0.4 to 30 mM. Compared to FIG. 12C and FIG. 12D, FIG. 12A and FIG. 12B both demonstrate that the printed sodium ionic electrode and potassium ionic electrode have excellent stability and less noisy performance with respect to the commercial reference electrode, wherein the linear sensitivities respectively are 61 and 50 mV/decade. In addition, to stabilize electrode current, the ionic sensor requires an additional Pt counter electrode for measurement in the buffer solution. This mainly attributes to the instability of the printed reference electrode resulting from the effect of the changes in environmental chloride ion (Cl⁻) concentrations on the miniaturized reference electrode.

Figure 13:
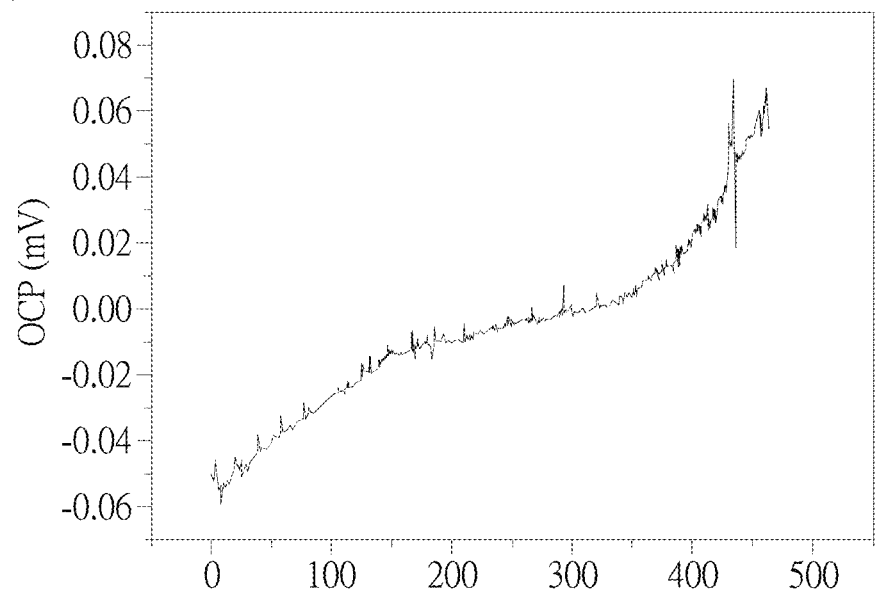
FIG. 13 depicts comparative results of the reference electrode covered with a PVC layer containing chloride ion or not with respect to a commercial reference electrode in the pH 7 buffer solution, wherein (a) depicts a result of a reference electrode not containing a PVC layer with respect to a commercial reference electrode; and (b) depicts a result of a reference electrode containing a PVC layer with respect to a commercial reference electrode.
Figure 13:
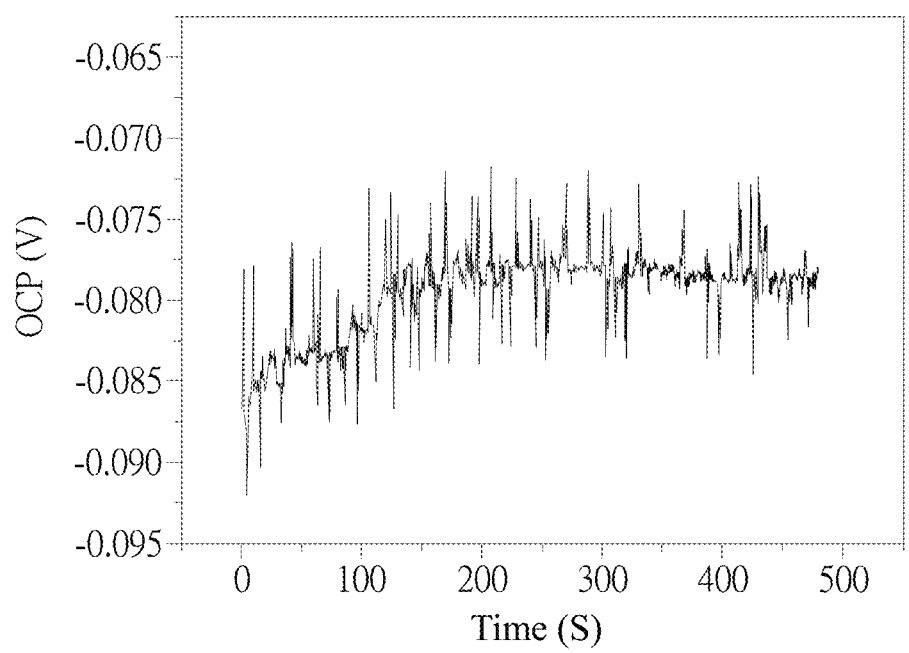

Please refer to FIG. 13 which depicts comparative results of the reference electrode covered with a PVC layer containing chloride ion or not with respect to a commercial reference electrode in the pH 7 buffer solution, wherein (a) depicts a result of a reference electrode not containing a PVC layer with respect to a commercial reference electrode; and (b) depicts a result of a reference electrode containing a PVC layer with respect to a commercial reference electrode. Compared to the commercial reference electrode, the reference electrode having a PVC layer containing chloride ion has greater stability than that in a condition without a PVC layer. The PVC layer containing chloride ion provides a stable oxidation-reduction reaction to maintain a stable potential. According to the results as mentioned above, the probe substrate of the present invention indeed accurately measures the concentrations of sodium ions and potassium ions, wherein the sensing range is also suitable for the use of detection on a human body.

Figure 14:
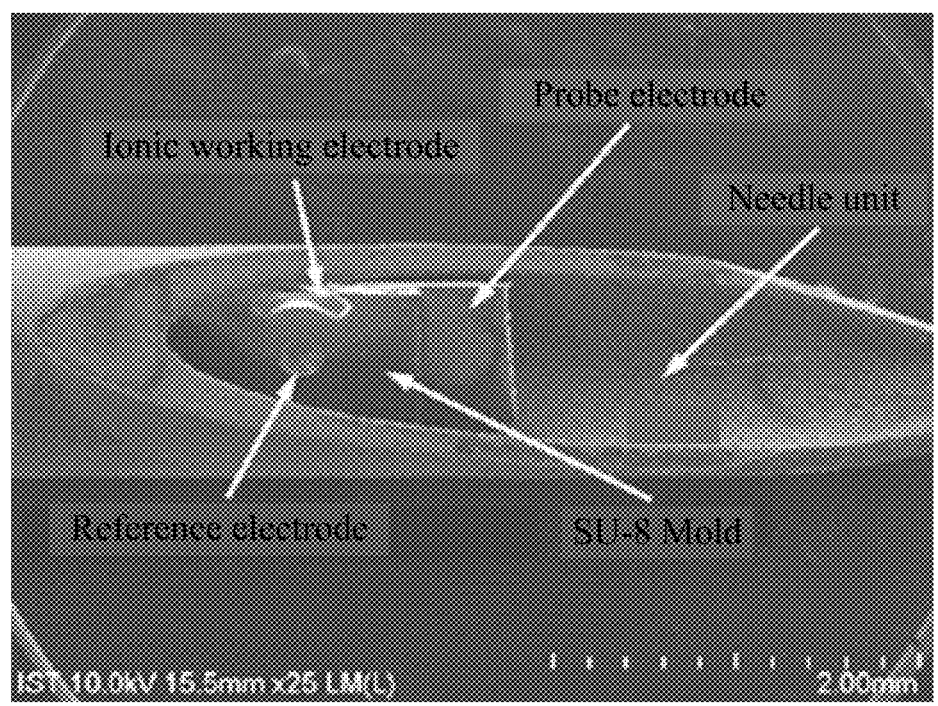
FIG. 14 depicts an electron microscopic image showing an integration of the probe substrate having flexibility with the needle unit of the present invention.

Please refer FIG. 14 which depicts an electron microscopic image showing an integration of the probe substrate 10 having flexibility with the needle unit 30 of the present invention. As shown, the probe substrate 10 is provided with a reference electrode RE and an ionic sensing electrode, which may be applied to monitoring sodium and potassium ions in deep muscles; however, the present invention is not limited thereto. That is, the user may also monitor the concentrations of other types of ion according to requirements, such as calcium ions, magnesium ions, and the like. According to the aforementioned embodiment, the miniaturized sensing probe of the present invention may print a temperature sensor, a pH sensor, or an ionic sensor on the probe substrate 10 by means of inkjet printing without performing other manufacturing processes, such as patterning a mask. Therefore, it is possible to immediately design a customized probe according to the needs of different patients even in an environment, such as a hospital.

Figure 15:
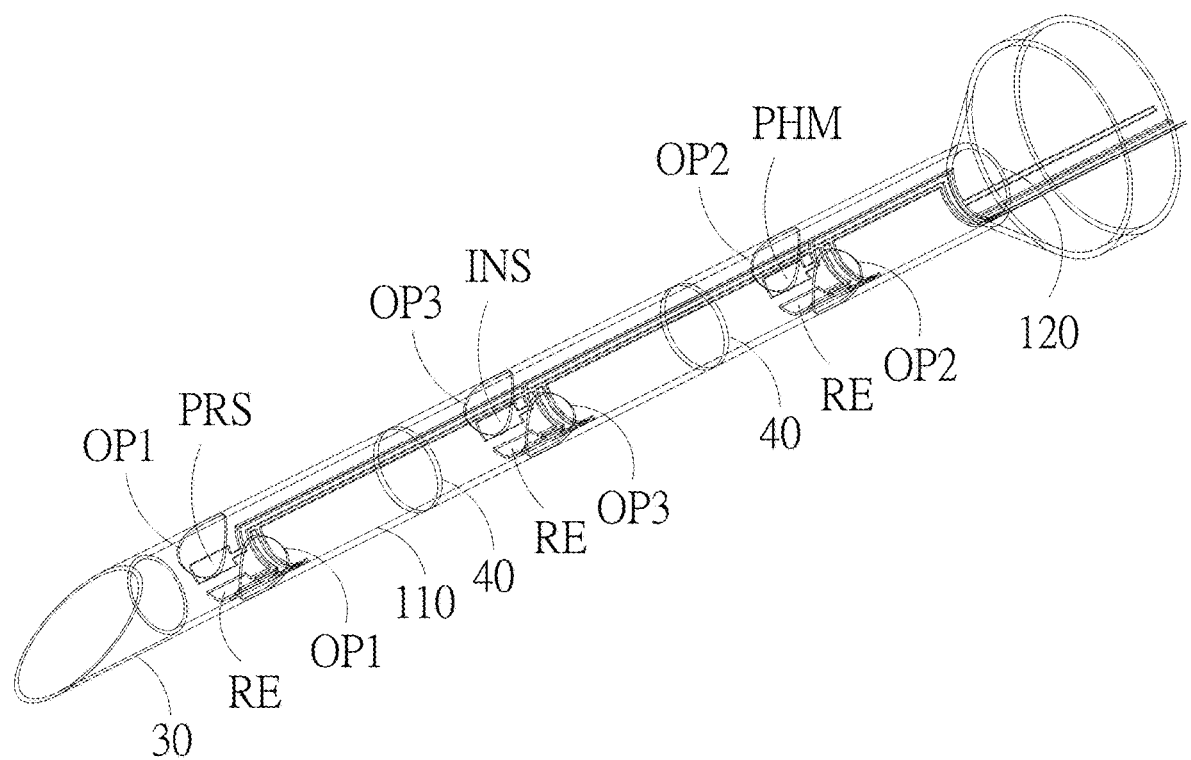
FIG. 15 depicts a schematic diagram of the miniaturized sensing probe according to the third embodiment of the present invention.

Please refer to FIG. 15 which depicts a schematic diagram of the miniaturized sensing probe according to a third embodiment of the present invention. The main difference between the third embodiment and the second embodiment lies in the fact that the probe substrate 10 disposed in the needle unit 30 may have a cylindrical shape, and the surface of the needle unit 30 may further include a plurality of openings. When the probe substrate 10 is disposed on the needle unit 30, the sensors on the probe part 110 may be disposed correspondingly to the positions of each of the openings; a waterproof element 40 is provided at an appropriate position between the openings OP. As shown in FIG. 15, the probe substrate 10 manufactured through a biocompatible and flexible material has a cylindrical shape with the surface thereon provided with a reference electrode RE, a pH sensor PHM, an ionic sensor INS, and a protein sensor PRS. In the present embodiment, the protein sensor PRS and the reference electrode RE may be disposed on the probe substrate 10 near the position of the opening of the needle unit 30 and corresponds to the position of the first opening OP1; the pH sensor PHM and the reference electrode RE may be disposed on the probe substrate 10 near the position of the circuit connection part 120 and corresponds to the position of the second opening OP2; and the ionic sensor INS and the reference electrode RE may be disposed at the positions between the pH sensor PHM and the protein sensor PRS and correspond to the position of the third opening OP3. Moreover, a waterproof element 40 is disposed between the first opening OP1 and the third opening OP3, as well as the third opening OP3 and the second opening OP2; the waterproof element 40 may separate the space between the probe substrate 10 and the needle unit 30 into several independent spaces to prevent fluid from flowing between the sensors respectively located in the first opening OP1, the second opening OP2, and the third opening OP3, thus achieving sensors in different positions being able to simultaneously sense values at different depth positions. In the present embodiment, the protein sensed by the protein sensor PRS may be lactic acid or troponin. In an alternative embodiment, the ionic sensors INS may be correspondingly disposed at the positions from the first opening OP1 to the third opening OP3 in order to detect ionic concentrations at different depth positions.

According to the third embodiment of the present invention, with the features of biocompatibility, the probe substrate 10 of the present invention, even placed in body tissues for a long time, may allow the probe of the present invention not to cause reactions such as allergy. In addition, since the probe substrate 10 has a cylindrical shape, the surface thereon at 360 degrees may be provided with sensors and wires, thus increasing the number of sensors disposed; meanwhile, some problems may be avoided, such as wires being overly dense, which causes failure to transmit signals effectively. By disposing a plurality of openings on the tube wall of the needle unit 30 and disposing the sensors, which is on the probe substrate 10, at the positions corresponding to the openings, the use of the miniaturized sensing probe of the present embodiment may expand the contact area of each sensor with tissue or blood, thus achieving better sensing sensitivity. In addition, a waterproof element 40 may be additionally disposed between the openings to prevent the fluid from flowing between the sensors, thus achieving the effectiveness for detecting tissues at different depth positions.

The present invention has been presented and illustrated with reference to the exemplary embodiments thereof. However, a person of ordinary skill in the art may conduct various alterations in terms of forms or details therein without departing from the scope of the present invention defined by the present claims as follows.

What is claimed is:
1. A miniaturized sensing probe, comprising:
a probe substrate comprising a probe part and a circuit connection part;
a needle unit used to accommodate the probe part of the probe substrate, wherein the needle unit has a plurality of openings disposed on a wall of the needle unit along a longitudinal direction of the needle unit;
a plurality of sensors respectively disposed on a plurality of positions, which are exposed by the plurality of the openings, on the probe part and electrically connecting the circuit connection part, wherein the plurality of sensors perform sensing functions when the needle unit is placed into an analyte and transmit a sensing signal through the circuit connection part; and a plurality of waterproof elements disposed between the openings to define a plurality of spaces for respectively accommodating the plurality of the sensors to prevent fluid from flowing between the plurality of the sensors.

2. The miniaturized sensing probe of claim 1, wherein the probe substrate is a silicon substrate or a flexible substrate.

3. The miniaturized sensing probe of claim 2, wherein the flexible substrate is a biocompatible substrate or a biodegradable substrate.

4. The miniaturized sensing probe of claim 2, wherein the plurality of the sensors comprise at least one of a temperature sensor, a pH sensor, and an ionic sensor when the probe substrate is a silicon substrate.

5. The miniaturized sensing probe of claim 2, wherein the plurality of the sensors comprise at least one of a temperature sensor, a pH sensor, an ionic sensor, and a protein sensor when the probe substrate is a flexible substrate.

6. The miniaturized sensing probe of claim 5, wherein a protein sensed by the protein sensor is lactic acid or troponin.

7. The miniaturized sensing probe of claim 1, wherein the needle unit has a caliber equal to or smaller than a caliber of a 23-gauge needle.

8. The miniaturized sensing probe of claim 1, wherein the plurality of sensors comprises a reference electrode and a polyvinyl chloride layer containing chloride ion is disposed on the reference electrode.

9. The miniaturized sensing probe of claim 1, wherein the plurality of sensors comprises a working electrode and a polyvinyl chloride layer containing chloride ion is disposed on the working electrode.

* * * * *